United States Patent
Yamamoto et al.

(10) Patent No.: US 8,871,973 B2
(45) Date of Patent: Oct. 28, 2014

(54) POLYALKYLENE GLYCOL PRODUCING CATALYST, AND METHOD FOR PRODUCING POLYALKYLENE GLYCOL USING SAME

(75) Inventors: Toshihide Yamamoto, Yokkaichi (JP); Yoshiaki Inoue, Yokkaichi (JP)

(73) Assignee: Tosoh Corporation, Shunan-Shi (JP)

( * ) Notice: Subject to any disclaimer, the term of this patent is extended or adjusted under 35 U.S.C. 154(b) by 847 days.

(21) Appl. No.: 13/120,852

(22) PCT Filed: Oct. 2, 2009

(86) PCT No.: PCT/JP2009/067252
§ 371 (c)(1),
(2), (4) Date: Mar. 24, 2011

(87) PCT Pub. No.: WO2010/038868
PCT Pub. Date: Apr. 8, 2010

(65) Prior Publication Data
US 2011/0178338 A1    Jul. 21, 2011

(30) Foreign Application Priority Data

Oct. 2, 2008 (JP) .................................. 2008-257286
Nov. 20, 2008 (JP) .................................. 2008-296909

(51) Int. Cl.
| | | |
|---|---|---|
| C07F 9/02 | (2006.01) | |
| C08G 65/26 | (2006.01) | |
| C07F 9/535 | (2006.01) | |
| C08G 65/10 | (2006.01) | |

(52) U.S. Cl.
CPC ........ C08G 65/2672 (2013.01); C08G 65/2675 (2013.01); C07F 9/5355 (2013.01); C08G 65/10 (2013.01)
USPC ........................................................ 564/12

(58) Field of Classification Search
CPC ................ C07F 9/02; C07F 9/36; C07F 9/46; C07F 9/5355
USPC ......................................................... 564/12
See application file for complete search history.

(56) References Cited

U.S. PATENT DOCUMENTS

| | | | |
|---|---|---|---|
| 3,829,505 A | 8/1974 | Herold | |
| 5,990,352 A | 11/1999 | Nobori et al. | |
| 6,153,794 A | 11/2000 | Funaki et al. | |
| 2007/0191567 A1 | 8/2007 | Tsuge et al. | |

FOREIGN PATENT DOCUMENTS

| | | |
|---|---|---|
| DE | 10 2006 010 034 A1 | 9/2007 |
| DE | 102006010034 A1 * | 9/2007 |
| EP | 0 239 973 A2 | 10/1987 |
| JP | 50-159595 A | 12/1975 |
| JP | 56-38323 A | 4/1981 |
| JP | 57-12026 A | 1/1982 |
| JP | 62-232433 A | 10/1987 |
| JP | 2-276821 A | 11/1990 |
| JP | 10-77289 A | 3/1998 |
| JP | 10-158388 A | 6/1998 |
| JP | 11-60722 A | 3/1999 |
| JP | 200-239288 A | 9/2000 |
| JP | 3497054 B2 | 2/2004 |
| JP | 2008201764 A * | 9/2008 |
| WO | WO 2006/043569 A1 | 4/2006 |

OTHER PUBLICATIONS

International Preliminary Report on Patentability dated Oct. 2, 2009.
International Search Report PCT/JP2009/067252 dated Dec. 8, 2009.

* cited by examiner

*Primary Examiner* — Sudhakar Katakam
*Assistant Examiner* — Kofi Adzamli
(74) *Attorney, Agent, or Firm* — Birch, Stewart, Kolasch & Birch, LLP

(57) ABSTRACT

To provide a catalyst composed of a salt of a phosphazenium cation and an active hydrogen compound anion, which can be easily synthesized, does not contain metal components at all, and does not leave any odor on a resulting product; a method for its production; an economical and efficient method for producing a polyalkylene oxide by means thereof; and a salt of a phosphazenium cation and an active hydrogen compound anion, represented by the following formula (2):

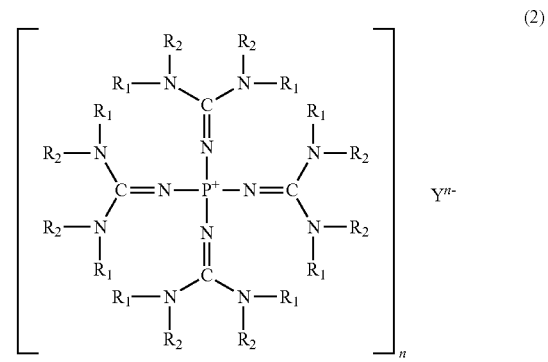

[in the above formula (2), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, n is a real number of from 1 to 8, and $Y^{n-}$ is an anion of an active hydrogen compound which is obtained by removing n protons from an active hydrogen compound Y] is used as a polyalkylene glycol producing catalyst.

19 Claims, No Drawings

POLYALKYLENE GLYCOL PRODUCING CATALYST, AND METHOD FOR PRODUCING POLYALKYLENE GLYCOL USING SAME

TECHNICAL FIELD

The present invention relates to a catalyst for economically producing a polyalkylene glycol by ring-opening polymerization of an alkylene oxide. A polyalkylene oxide is reacted with an isocyanate compound to form an important polymer to be used as e.g. a raw material for e.g. a polyurethane foam or elastomer, or a surfactant.

BACKGROUND ART

As a catalyst for producing a polyalkylene oxide by ring-opening polymerization of an alkylene oxide, for example, an active hydrogen compound and a compound represented by $Zn_3[Fe(CN)_6]_2 \cdot H_2O \cdot dioxane$ are known (e.g. Patent Document 1). Further, it is known to use a zinc hexacyanocobaltate complex as the catalyst (e.g. Patent Document 2). It is further known to use, as the catalyst, a product obtained by adding a solution of diethylzinc in hexane to a dispersion obtained by adding 1,4-butanediol and a non-ionic surfactant to a slurry of fumed silica in hexane (e.g. Patent Document 3). However, each of the catalysts disclosed in these documents, contains a special metal component, and if such a metal component remains in the formed polyalkylene oxide, it adversely affects the reaction during the production of a polyurethane or the physical properties of the polyurethane. Accordingly, in the production of a polyalkylene oxide, a special method or cumbersome steps are required to sufficiently remove such a metal component.

On the other hand, as a catalyst containing no metal, patent Document 4 discloses a catalyst which is combination of an alkane polyol being an active hydrogen compound and an ether adduct of boron trifluoride. However, it is known that a peculiar impurity in the polymer obtainable by this catalyst system adversely affects the physical properties of a polyurethane, and cumbersome steps are required to sufficiently remove such an impurity. Further, Patent Document 5 discloses to obtain a polymer of an alkylene oxide by using an alcohol and an amino phenol as catalysts, and Patent Document 6 discloses to polymerize propylene oxide by using sorbitol and tetramethyl ammonium hydroxide. However, in each of the cases where the catalysts disclosed in these documents are used, the polymerization activity is not sufficient, and there is a problem such that an amine type odor remains.

Further, it is known that a phosphazenium salt of an active hydrogen compound represented by the following formula:

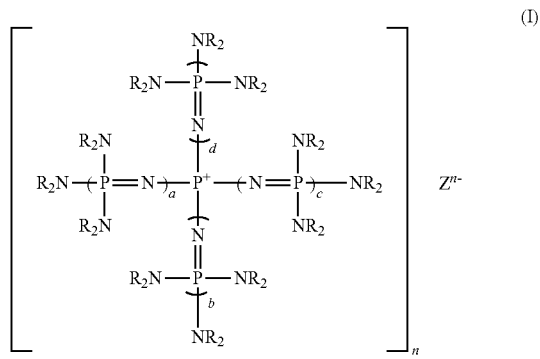
(I)

[in the above formula, n is an integer of from 1 to 8 and represents the number of phosphazenium cations, $Z^{n-}$ is an n-valent active hydrogen compound anion in the form obtained by removing n protons from an active hydrogen compound having at most 8 active hydrogen atoms on oxygen atoms or nitrogen atoms, and each of a, b, c and d is a positive integer of at most 3, or 0, provided that all of them are not simultaneously 0, and R's are the same or different $C_{1-10}$ hydrocarbon groups, provided that two R's on the same nitrogen atom may be bonded to each other to form a ring structure] is obtained by reacting a salt of a phosphazenium cation and an inorganic anion, represented by the following formula:

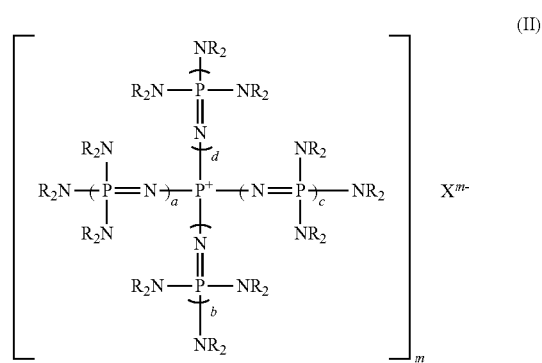
(II)

[in the above formula, m is an integer of from 1 to 3 and represents the number of phosphazenium cations, $X^{m-}$ is an m-valent inorganic anion, each of a, b, c and d is a positive integer of at most 3, or 0, provided that all of them are not simultaneously 0, and R's are the same or different $C_{1-10}$ hydrocarbon groups, provided that two R's on the same nitrogen atom may be bonded to each other to form a ring structure] with an alkali metal salt of an active hydrogen compound represented by $M^+_n Z^{n-}$ (wherein $M^+_n$ represents n alkali metal cations, n is an integer of from 1 to 8, and $Z^{n-}$ is a n-valent active hydrogen compound anion in the form obtained by removing n protons from an active hydrogen compound having at most 8 active hydrogen atoms on oxygen atoms or nitrogen atoms and is the same as $Z^{n-}$ in the above phosphazenium salt), and the above phosphazenium salt is useful as a catalyst for ring-opening polymerization of propylene oxide (e.g. Patent Document 7). However, this phosphazenium salt has had an economical problem, since its production process requires many steps, and the operation is cumbersome.

Further, it has been reported that a nitrogen-containing phosphonium salt represented by the following formula (III):

(in the formula, n=2 to 4, m=0, 1 or 2, n+m=4, R is —N=C(NR$_1$R$_2$)(NR$_3$R$_4$), Y is —N(R$_5$)(R$_6$), each of R$_1$ to R$_6$ which are independent of one another, is a $C_{1-10}$ cyclic, aliphatic or aromatic hydrocarbon which may have a substituent, and contains at least one hetero atom or at least one chiral center, or (—CH$_2$—CH$_2$—O—)$_o$—CH$_2$CH$_2$—Oalk (o=1 to 12), and X is an anion obtainable from an inorganic or organic acid having O, N or S bonded to active oxygen) is useful as a non-metallic catalyst for e.g. a halogen-exchange reaction or a phase-transfer catalytic reaction, production of a polyalkylene polyol polymer, polymerization of a lactam, a polyurethane or halogenated hydrocarbon polymerization reaction, or a halogen-deprotection reaction (e.g. Patent Document 8).

However, Patent Document 8 does not disclose any example for preparation of a polyalkylene polyol and teaches nothing about how to prepare a polyalkylene polyol by means of a nitrogen-containing phosphonium salt of the above formula (III) or what types of a polyalkylene polyol is thereby prepared.

PRIOR ART DOCUMENTS

Patent Documents

Patent Document 1: U.S. Pat. No. 3,829,505
Patent Document 2: JP-A-2-276821
Patent Document 3: JP-A-62-232433
Patent Document 4: JP-A-50-159595
Patent Document 5: JP-A-57-12026
Patent Document 6: JP-A-56-38323
Patent Document 7: Japanese Patent No. 3,497,054 (JP-A-10-77289)
Patent Document 8: German Patent No. 102006010034

DISCLOSURE OF INVENTION

Technical Problem

The present invention has been made in view of the above-described technical background, and its object is to provide a catalyst composed of a salt of a phosphazenium cation and an active hydrogen compound anion, which can be easily synthesized, does not contain metal components at all, and does not leave any odor on a product; a method for its production; and an economical and efficient method for producing a polyalkylene oxide by means thereof.

Solution to Problem

The present inventors have conducted an extensive study to accomplish the above object and as a result, have found it possible to produce extremely efficiently and economically a polyalkylene glycol by ring-opening polymerization of an alkylene oxide by means of a catalyst obtained by heat treatment of a specific phosphazenium salt and an active hydrogen compound, and have finally accomplished the present invention.

That is, the present invention provides a catalyst for producing a polyalkylene glycol and a method for producing a polyalkylene glycol by means thereof, as described below.

[1] A polyalkylene glycol producing catalyst which is composed of a salt of a phosphazenium cation and an active hydrogen compound anion, represented by the following formula (2):

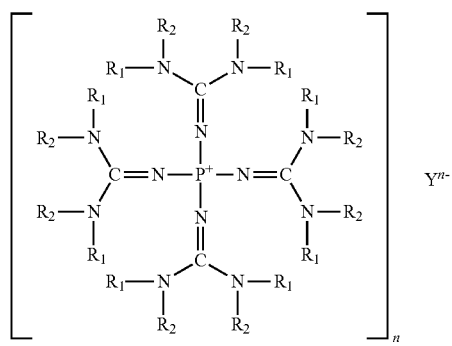

(2)

[in the above formula (2), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, n is a real number of from 1 to 8, and $Y^{n-}$ is an anion of an active hydrogen compound which is obtained by removing n protons from an active hydrogen compound Y].

[2] The polyalkylene glycol producing catalyst according to the above [1], wherein in the phosphazenium cation represented by the formula (2), each of $R_1$ and $R_2$ is a methyl group, or $R_1$ is a methyl group or an isopropyl group and $R_2$'s are bonded to each other to form a dimethylene group thereby to form a ring structure.

[3] The polyalkylene glycol producing catalyst according to the above [1] or [2], wherein the active hydrogen compound Y is water or a compound selected from an organic compound having a partial structural formula of —OH or —NH—.

[4] The polyalkylene glycol producing catalyst according to the above [3], wherein the organic compound having a partial structural formula of —OH is one or more members selected from the group consisting of a $C_{1-20}$ alcohol, a $C_{2-20}$ polyhydric alcohol having from 2 to 8 hydroxy groups, a saccharide or its derivative, and a polyalkylene oxide having from 2 to 8 terminals, having from 1 to 8 hydroxy groups at the terminals and having a number average molecular weight of from 200 to 20,000.

[5] The polyalkylene glycol producing catalyst according to the above [3], wherein the organic compound having a partial structural formula of —NH— is one or more members selected from the group consisting of a $C_{2-20}$ polyvalent amine having 2 or 3 primary or secondary amino groups, a $C_{4-10}$ saturated cyclic secondary amine, and a $C_{4-10}$ cyclic polyvalent amine having 2 or 3 secondary amino groups.

[6] A method for producing the polyalkylene glycol producing catalyst as defined in any one of the above [1] to [5], which comprises mixing a phosphazenium salt represented by the following formula (1):

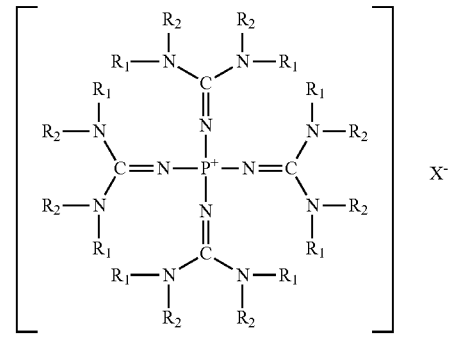

(1)

[in the above formula (1), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, and X⁻ is a hydroxy anion, an alkoxy anion or a carboxy anion] and an active hydrogen compound Y, followed by heat treatment.

[7] The method for producing the polyalkylene glycol producing catalyst according to the above [6], wherein in the phosphazenium salt represented by the formula (1), each of $R_1$ and $R_2$ is a methyl group, or $R_1$ is a methyl group or an isopropyl group and $R_2$'s are bonded to each other to form a dimethylene group thereby to form a ring structure.

[8] The method for producing the polyalkylene glycol producing catalyst according to the above [6] or [7], wherein X⁻ in the phosphazenium salt represented by the formula (1) is one or more anions selected from the group consisting of a hydroxy anion, an alkoxy anion derived from a $C_{1-4}$ saturated alkyl alcohol or phenol, and a carboxy anion derived from a $C_{2-4}$ carboxylic acid.

[9] The method for producing the polyalkylene glycol producing catalyst according to any one of the above [6] to [8], wherein X⁻ in the phosphazenium salt represented by the formula (1) is a hydroxy anion.

[10] The method for producing the polyalkylene glycol producing catalyst according to any one of the above [6] to [9], wherein the active hydrogen compound Y is water or a compound selected from an organic compound having a partial structural formula of —OH or —NH—.

[11] The method for producing the polyalkylene glycol producing catalyst according to the above [10], wherein the organic compound having a partial structural formula of —OH is one or more members selected from the group consisting of a $C_{1-20}$ alcohol, a $C_{2-20}$ polyhydric alcohol having from 2 to 8 hydroxy groups, a saccharide or its derivative, and a polyalkylene oxide having from 2 to 8 terminals, having from 1 to 8 hydroxy groups at the terminals and having a number average molecular weight of from 200 to 20,000.

[12] The method for producing the polyalkylene glycol producing catalyst according to the above [10], wherein the organic compound having a partial structural formula of —NH— is one or more members selected from the group consisting of a $C_{2-20}$ polyvalent amine having 2 or 3 primary or secondary amino groups, a $C_{4-10}$ saturated cyclic secondary amine, and a $C_{4-10}$ cyclic polyvalent amine having 2 or 3 secondary amino groups.

[13] The method for producing the polyalkylene glycol producing catalyst according to any one of the above [6] to [12], which comprises mixing the phosphazenium salt represented by the formula (1) and the active hydrogen compound Y within such a range that the active hydrogen compound Y is from 0.2 to 1,000 mol per 1 mol of the phosphazenium salt, followed by heat treatment.

[14] A method for producing a polyalkylene glycol, which comprises subjecting an alkylene oxide to ring-opening polymerization in the presence of the polyalkylene glycol producing catalyst as defined in any one of the above [1] to [5].

[15] A method for producing a polyalkylene glycol, which comprises subjecting an alkylene oxide to ring-opening polymerization in the presence of the polyalkylene glycol producing catalyst obtained by the method as defined in any one of the above [6] to [13].

[16] A method for producing a polyalkylene glycol, which comprises mixing a phosphazenium salt represented by the following formula (1):

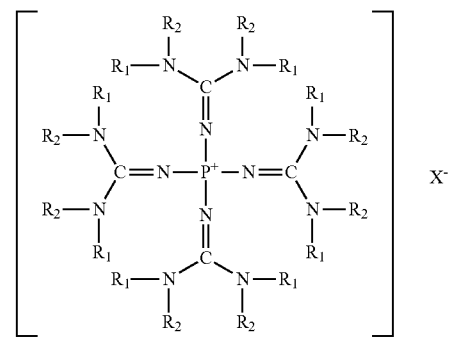

[in the above formula (1), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, and X⁻ is a hydroxy anion, an alkoxy anion or a carboxy anion] and an active hydrogen compound Y, followed by heat treatment, and then adding an alkylene oxide and subjecting the alkylene oxide to ring-opening polymerization.

[17] The method for producing a polyalkylene glycol according to any one of the above [14] to [16], wherein the alkylene oxide is one or more members selected from the group consisting of ethylene oxide, propylene oxide, 1,2-butylene oxide and styrene oxide.

[18] A polyalkylene glycol having a total unsaturation value of at most 0.07 meq./g and a molecular weight distribution (Mw/Mn) of at most 1.1, obtained by the method as defined in any one of the above [14] to [17].

[19] A polyalkylene glycol having a hydroxy value of at most 60 mgKOH/g and a number average molecular weight within a range of from 3,000 to 50,000, obtained by the method as defined in any one of the above [14] to [17].

Advantageous Effects of Invention

The polyalkylene glycol producing catalyst of the present invention does not use a special metal component and thus requires no special method or cumbersome steps to sufficiently remove such a metal component.

Further, in the method for producing a polyalkylene glycol using such a polyalkylene glycol producing catalyst of the present invention, the temperature control during the reaction of an alkylene oxide becomes easy, and it is possible to produce a polyalkylene oxide having a narrow molecular weight distribution, a high molecular weight and a low total unsaturation value simply and efficiently without leaving an odor.

Thus, the present invention is industrially very useful.

DESCRIPTION OF EMBODIMENTS

The polyalkylene glycol producing catalyst of the present invention is obtained by heat-treating a phosphazenium salt represented by the following formula (1):

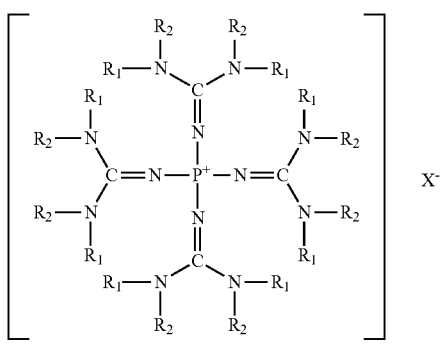

(1)

[in the above formula (1), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, and $X^-$ is a hydroxy anion, an alkoxy anion or a carboxy anion] and an active hydrogen compound Y. The mixing ratio at that time is preferably within a range such that the active hydrogen compound Y is from 0.2 to 1,000 mol per 1 mol of the phosphazenium salt represented by the above formula (1). If the mixing ratio is smaller than this range, although a high activity may be obtained, control of the reaction heat tends to be difficult, and the physical properties of the obtainable polyalkylene glycol tend to deteriorate. On the other hand, if the mixing ratio is larger than this range, there may be a case where no adequate activity can be obtained. With a view to securing a high activity, the mixing ratio is preferably within a range of from 1 to 500 mol. Further, from such a viewpoint that the reaction temperature can easily be controlled, the mixing ratio is more preferably within a range of from 10 to 300 mol.

The catalyst of the present invention is composed of a salt of a phosphazenium cation and an active hydrogen compound anion, represented by the following formula (2):

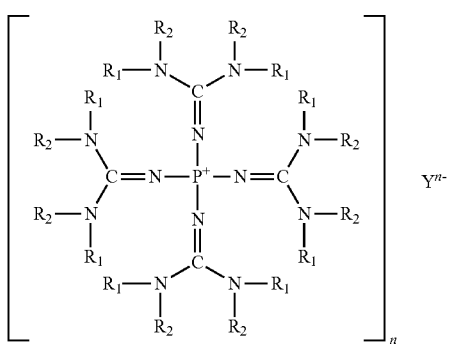

(2)

[in the above formula (2), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, n is a real number of from 1 to 8, and $Y^{n-}$ is an anion of an active hydrogen compound which is obtained by removing n protons from an active hydrogen compound Y], to be formed by the heat treatment of the phosphazenium salt represented by the above formula (1) and the active hydrogen compound. Here, n is preferably a real number of larger than 1 and at most 6.

In the present invention, the substituent $R_1$ or $R_2$ in the above formula (1) or (2) each independently is a $C_{1-10}$ alkyl group, an unsubstituted or substituted $C_{6-10}$ phenyl group, or an unsubstituted or substituted $C_{6-10}$ phenylalkyl group.

Specifically, an aliphatic or aromatic hydrocarbon group such as a methyl group, an ethyl group, a n-propyl group, an isopropyl group, a n-butyl group, a sec-butyl group, a tert-butyl group, a 2-butyl group, a 1-pentyl group, a 2-pentyl group, a 3-pentyl group, a 2-methyl-1-butyl group, an isopentyl group, a tert-pentyl group, a 3-methyl-2-butyl group, a neopentyl group, a n-hexyl group, a 4-methyl-2-pentyl group, a cyclopentyl group, a cyclohexyl group, a 1-heptyl group, a 3-heptyl group, a 1-octyl group, a 2-octyl group, a 2-ethyl-1-hexyl group, a 1,1-dimethyl-3,3-dimethylbutyl group, a nonyl group, a decyl group, a phenyl group, a 4-toluyl group, a benzyl group, a 1-phenylethyl group or a 2-phenylethyl group may be exemplified. Among them, a $C_{1-10}$ aliphatic hydrocarbon group such as a methyl group, an ethyl group, a n-propyl group, an isopropyl group, a tert-butyl group, a tert-pentyl group or a 1,1-dimethyl-3,3-dimethylbutyl group, is preferred, and a methyl group is particularly preferred.

In the present invention, with respect to the substituents $R_1$ and $R_2$ in the above formula (1) or (2), $R_1$ and $R_2$, or $R_2$'s, may be bonded to each other to form a ring structure. Specifically, they may be bonded to form a dimethylene group, a trimethylene group, a tetramethylene group, a pentamethylene group or a hexamethylene group, preferably a dimethylene group, a trimethylene group or a tetramethylene group. With respect to the substituents $R_1$ and $R_2$, for example, it is preferred that each of $R_1$ and $R_2$ is a methyl group, or $R_1$ is a methyl group or an isopropyl group and in the moiety of —N=C[—$NR_1R_2]_2$, $R_2$'s are bonded to each other to form a dimethylene group thereby to form a ring structure.

In the present invention, $X^-$ in the above formula (1) is one or more anions selected from the group consisting of a hydroxy anion, a hydrocarbon anion, a hydrogencarbonate ion, an alkoxy anion and a carboxy anion.

In the present invention, among such $X^-$ in the formula (1), the alkoxy anion may, for example, be an alkoxy anion derived from a $C_{1-8}$ alcohol such as methanol, ethanol, n-propanol, isopropanol, allyl alcohol, n-butanol, sec-butanol, tert-butanol, cyclohexanol, 2-heptanol, 1-octanol or phenol. Whereas, the carboxy anion may, for example, be a carboxy anion derived from a $C_{1-6}$ carboxylic acid such as formic acid, acetic acid, propionic acid, butyric acid, isobutyric acid or caproic acid.

In the present invention, more preferred among them is a hydroxy anion; a methoxy anion or an ethoxy anion as an alkoxy anion; or an acetic anion as a carboxy anion.

In the present invention, as the phosphazenium salt represented by the formula (1), one type may be used alone, or two or more types may be used as mixed.

In the present invention, the active hydrogen compound Y is a compound having active hydrogen and is water or a compound selected from an organic compound having a partial structural formula of —OH or —NH—.

The organic compound having a partial structural formula of —OH to be used in the present invention may, for example, be a $C_{1-20}$ carboxylic acid such as formic acid, acetic acid, propionic acid, butyric acid, isobutyric acid, lauric acid, stearic acid, oleic acid, phenylacetic acid, dihydrocinnamic acid, cyclohexanecarboxylic acid, benzoic acid, p-methylbenzoic acid or 2-carboxynaphthalene;

a $C_{2-20}$ polycarboxylic acid having from 2 to 6 carboxy groups, such as oxalic acid, malonic acid, succinic acid, maleic acid, fumaric acid, adipic acid, itaconic acid, butanetetracarboxylic acid, phthalic acid, isophthalic acid, terephthalic acid, trimellitic acid or pyromellitic acid;

a carbamic acid such as N,N-diethylcarbamic acid, N-carboxypyrrolidone, N-carboxyaniline or N,N'-dicarboxy-2,4-toluenediamine;

a $C_{1-20}$ alcohol such as methanol, ethanol, n-propanol, isopropanol, n-butyl alcohol, sec-butyl alcohol, tert-butyl alcohol, isopentyl alcohol, tert-pentyl alcohol, n-octyl alcohol, lauryl alcohol, cetyl alcohol, cyclopentanol, cyclohexanol, allyl alcohol, crotyl alcohol, methyl vinyl carbinol, benzyl alcohol, 1-phenylethyl alcohol, triphenyl carbinol or cinnamyl alcohol;

a $C_{2-20}$ polyhydric alcohol having from 2 to 8 hydroxy groups, such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerol, diglycerol, trimethylolmelamine, pentaerythritol or dipentaerythritol;

a saccharide such as glucose, sorbitol, dextrose, fructose or sucrose, or its derivative;

a $C_{6-20}$ aromatic compound having from 1 to 3 hydroxy groups, such as phenol, 2-naphthol, 2,6-dihydroxynaphthalene or bisphenol A; or a polyalkylene oxide having from 2 to 8 terminals, having from 1 to 8 hydroxy groups at the terminals and having a number average molecular weight of from 200 to 50,000, which is, for example, a polyethylene oxide, a polypropylene oxide or a copolymer thereof.

Further, in the present invention, an organic compound having a partial structural formula of —OH other than those exemplified above may be used unless such use is against the purpose of the present invention.

Whereas, the organic compound having a partial structural formula of —NH— to be used in the present invention may, for example, be a $C_{1-20}$ aliphatic or aromatic primary amine such as methylamine, ethylamine, n-propylamine, isopropylamine, n-butylamine, isobutylamine, sec-butylamine, tert-butylamine, cyclohexylamine, benzylamine, β-phenylethylamine, aniline, o-toluidine, m-toluidine, or p-toluidine;

a $C_{2-20}$ aliphatic or aromatic secondary amine such as dimethylamine, methylethylamine, diethylamine, di-n-propylamine, ethyl-n-butylamine, methyl-sec-butylamine, dipentylamine, dicyclohexylamine, N-methylaniline or diphenylamine;

a $C_{2-20}$ polyvalent amine having 2 or 3 primary or secondary amino groups, such as ethylene diamine, di(2-aminoethyl)amine, hexamethylene diamine, 4,4'-diaminodiphenylmethane, melamine, tri(2-aminoethyl)amine, N,N'-dimethylethylene diamine or di(2-methylaminoethyl)amine;

a $C_{4-20}$ saturated cyclic secondary amine such as pyrrolidine, piperidine, morpholine or 1,2,3,4-tetrahydroquinoline;

a $C_{4-20}$ unsaturated cyclic secondary amine such as 3-pyroline, pyrrole, indole, carbazole, imidazole, pyrazole or purine;

a $C_{4-20}$ cyclic polyvalent amine containing 2 or 3 primary amino groups, such as piperazine, pyrazine or 1,4,7-triazacyclononane;

a $C_{2-20}$ unsubstituted or N-mono-substituted acid amide such as acetamide, propionamide, N-methylpropion amide, N-methylbenzoic acid amide or N-ethylstearic acid amide;

a cyclic amide having a 5 to 7-membered ring, such as 2-pyrrolidone or ε-caprolactam; or an imide of a $C_{4-10}$ dicarboxylic acid, such as succinic acid imide, maleic acid imide or phthalimide.

Further, in the present invention, an organic compound having a partial structural formula of —NH— other than those exemplified above may be used so long as such use is not against the purpose of the present invention.

The organic compound having a partial structural formula of —OH to be used in the present invention may preferably be, for example, a $C_{1-20}$ alcohol such as methanol, ethanol, n-propanol, isopropanol, n-butyl alcohol, sec-butyl alcohol, tert-butyl alcohol, isopentyl alcohol, tert-pentyl alcohol, n-octyl alcohol, lauryl alcohol, cetyl alcohol, cyclopentanol, cyclohexanol, allyl alcohol, crotyl alcohol, methyl vinyl carbinol, benzyl alcohol, 1-phenylethyl alcohol, triphenylcarbinol or cinnamyl alcohol;

a $C_{2-20}$ polyhydric alcohol having from 2 to 8 hydroxy groups, such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerol, diglycerol, pentaerythritol or dipentaerythritol; a saccharide such as glucose, sorbitol, dextrose, fructose or sucrose or its derivative; or a polyalkylene oxide having from 2 to 8 terminals, having from 1 to 8 hydroxy groups at the terminals and having a number average molecular weight of from 200 to 50,000, which is a polyethylene oxide, a polypropylene oxide or a copolymer thereof.

Further, in the catalyst of the present invention or in the method for its production, the organic compound having a partial structural formula of —NH— may preferably be, for example, a $C_{2-20}$ polyvalent amine having 2 or 3 primary or secondary amino groups, such as ethylenediamine, di(2-aminoethyl)amine, hexamethylenediamine, 4,4'-diaminodiphenylmethane, tri(2-aminoethyl)amine, N,N'-dimethylethylenediamine, N,N'-diethylethylenediamine or di(2-methylaminoethyl)amine; a $C_{4-10}$ saturated cyclic secondary amine such as pyrrolidine, piperidine, morpholine or 1,2,3,4-tetrahydroquinoline; or a $C_{4-10}$ cyclic polyvalent amine having 2 or 3 secondary amino groups, such as piperazine, pyrazine or 1,4,7-triazacyclononane.

In the present invention, among these active hydrogen compounds, more preferred is an organic compound having a partial structural formula of —OH, such as a $C_{2-20}$ polyhydric alcohol having from 2 to 8 hydroxy groups, such as ethylene glycol, propylene glycol, 1,4-butanediol, trimethylolpropane, glycerol, pentaerythritol or dipentaerythritol; a saccharide such as glucose, sorbitol, dextrose, fructose or sucrose, or its derivative; or a polyalkylene oxide having from 2 to 6 terminals, having from 2 to 6 hydroxy groups at the terminals and having a number average molecular weight of from 200 to 10,000, which is a polyethylene oxide, a polypropylene oxide or a copolymer thereof.

In the method for producing the catalyst of the present invention, the heat treatment is carried out usually under a reduced pressure of at most 1.3 kPa, preferably within a range of from 1.0 to 0.05 kPa, more preferably within a range of from 0.5 to 0.01 kPa. If the reduced pressure degree is low, not only the heat treatment time tends to be long, but also formation of the desired salt of a phosphazenium cation and an active hydrogen compound anion will not sufficiently proceed, whereby no adequate polymerization activity may be obtainable. On the other hand, if the reduced pressure degree is higher than necessary, such becomes uneconomical although there may be no influence over the formation of the salt of a phosphazenium cation and an active hydrogen compound anion.

In the method for producing the catalyst of the present invention, the treating temperature in the heat treatment is usually at a temperature of at least 60° C., preferably at a temperature within a range of from 70 to 110° C., more preferably from 80 to 100° C. If the treating temperature if low, formation of the desired salt of a phosphazenium cation and an active hydrogen compound anion will not sufficiently proceed, whereby no adequate polymerization activity will be obtainable, and on the other hand, if the treating temperature is too high, deterioration of the polymerization activity may be led due to thermal degradation of the active hydrogen compound or the formed salt of a phosphazenium cation and an active hydrogen compound anion.

In the production of the catalyst of the present invention, the time required for the heat treatment is not particularly limited, but it is usually sufficient when the heat treatment is carried out for at least 1 hour, preferably from 2 to 10 hours, more preferably from 3 to 6 hours. If the treating time is short, formation of the desired salt of a phosphazenium cation and an active hydrogen compound anion will not sufficiently proceed, thus leading to deterioration of the polymerization activity, and on the other hand, if the treating time is longer than necessary, such is not only uneconomical but also likely to lead to deterioration of the polymerization activity due to thermal degradation of the active hydrogen compound or the formed salt of a phosphazenium cation and an active hydrogen compound anion.

At the time when the salt of a phosphazenium cation and an active hydrogen compound anion, represented by the above formula (2) is led from the phosphazenium salt represented by the above formula (1) and the active hydrogen compound Y, the active hydrogen compound is used usually in excess, and the excess amount of the active hydrogen compound will remain as it is, and in addition, water, an alcohol or a carboxylic acid will be formed as a byproduct depending upon the type of the phosphazenium salt. In the method for producing the catalyst of the present invention, such a byproduct may be removed prior to the polymerization reaction of an alkylene oxide compound. As such a method, a method of distillation under heating or under reduced pressure, a method of supplying an inert gas or a method of employing an adsorbing agent may, for example, be employed depending upon the nature of such a byproduct.

In the method for producing the catalyst of the present invention, the method for producing the phosphazenium salt represented by the above formula (1) is not particularly limited. However, it may, for example, be produced by reacting a phosphorus pentahalide represented by the following formula (3):

P—X$_5$                                                  (3)

[in the formula (3), X is a chlorine atom or a bromine atom] with 4 equivalents of a guanidine derivative represented by the following formula (4):

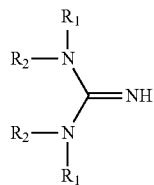

(4)

[in the formula (4), each of R$_1$ and R$_2$ which are independent of each other, is a C$_{1-10}$ alkyl group, an unsubstituted or substituted C$_{6-10}$ phenyl group, or an unsubstituted or substituted C$_{6-10}$ phenylalkyl group, provided that R$_1$ and R$_2$, or R$_2$'s, may be bonded to each other to form a ring structure].

The phosphorus pentahalide represented by the above formula (3) to be used in the above reaction may be phosphorus pentachloride or phosphorus pentabromide, preferably phosphorus pentachloride.

Each of substituents R$_1$ and R$_2$ of the guanidine derivative represented by the above formula (4) to be used in the above reaction, which are independent of each other, is a C$_{1-10}$ alkyl group, an unsubstituted or substituted C$_{6-10}$ phenyl group, or an unsubstituted or substituted C$_{6-10}$ phenylalkyl group, and R$_1$ and R$_2$, or R$_2$'s, may be bonded to each other to form a ring structure.

In the above reaction, the substituents R$_1$ and R$_2$ in the above formula (4) are not particularly limited. However, specifically, each of them independently is a C$_{1-10}$ alkyl group, an unsubstituted or substituted C$_{6-10}$ phenyl group, or an unsubstituted or substituted C$_{6-10}$ phenylalkyl group. Specifically, an aliphatic or aromatic hydrocarbon group is exemplified such as a methyl group, an ethyl group, a n-propyl group, an isopropyl group, a n-butyl group, a sec-butyl group, a tea-butyl group, a 2-butyl group, a 1-pentyl group, a 2-pentyl group, a 3-pentyl group, a 2-methyl-1-butyl group, an isopentyl group, a tert-pentyl group, a 3-methyl-2-butyl group, a neopentyl group, a n-hexyl group, a 4-methyl-2-pentyl group, a cyclopentyl group, a cyclohexyl group, a 1-heptyl group, a 3-heptyl group, a 1-octyl group, a 2-octyl group, a 2-ethyl-1-hexyl group, a 1,1-dimethyl-3,3-dimethylbutyl group, a nonyl group, a decyl group, a phenyl group, a 4-toluyl group, a benzyl group, a 1-phenylethyl group or a 2-phenylethyl group. Among them, a C$_{1-10}$ aliphatic hydrocarbon group such as a methyl group, an ethyl group, a n-propyl group, an isopropyl group, a tert-butyl group, a tert-pentyl group or a 1,1-dimethyl-3,3-dimethylbutyl group is preferred, and a methyl group is particularly preferred.

In the above reaction, with respect to the substituents R$_1$ and R$_2$ in the above formula (4), R$_1$ and R$_2$, or R$_2$'s, may be bonded to each other to form a ring structure. Specifically, they may be bonded to form, for example, a dimethylene group, a trimethylene group, a tetramethylene group, a pentamethylene group or a hexamethylene group, preferably a dimethylene group, a trimethylene group or a tetramethylene group. The guanidine derivative represented by the formula (4) may preferably be, for example, one wherein each of R$_1$ and R$_2$ is a methyl group, or R$_1$ is a methyl group or an isopropyl group and R$_2$'s are bonded to each other to form a dimethylene group thereby to form a ring structure.

The amount of the guanidine derivative represented by the above formula (4) to be used, is usually within a range of from 6 to 20 mol, preferably within a range of from 8 to 12 mol, per 1 mol of the phosphorus pentahalide. If the amount of the guanidine derivative to be used, is small, the amount of the desired phosphazenium salt tends to substantially decrease, and on the other hand, if the amount to be used is too much, such will be uneconomical although such will not substantially influence the reaction.

In the above reaction, the solvent to be used for the reaction of the phosphorus pentahalide with the guanidine derivative may be any solvent so long as it will not hinder the reaction and is not particularly limited. It may, for example, be an aromatic hydrocarbon such as benzene, toluene or xylene, or a halogenated aromatic hydrocarbon such as chlorobenzene or o-dichlorobenzene. Preferred is an aromatic hydrocarbon such as toluene or xylene. Such solvents may be used alone or in combination as a mixture of two or more of them. It is preferred that the reaction proceeds in a uniform state, but there is no problem even if the reaction proceeds in a non-uniform state. Further, the solvent to be used is preferably used after subjected to dehydration treatment.

In the above reaction, the amount of the solvent to be used for the reaction of the phosphorus pentahalide with the guanidine derivative is usually within a range of from 0.1 to 80 L (liter), preferably within a range of from 0.5 to 40 L, more preferably within a range of from 1 to 20 L, per 1 mol of the phosphorus pentahalide. If the amount of the solvent is small, control of the temperature tends to be difficult, and a side-reaction may be induced, and on the other hand, if the amount of the solvent is too much, not only the treatment after the reaction tends to be cumbersome, but also such is uneconomical.

In the above reaction, the reaction of the phosphorus pentahalide with the guanidine derivative is carried out usually in an atmosphere of an inert gas such as helium, nitrogen or argon.

In the above reaction, the reaction temperature in the reaction of the phosphorus pentahalide with the guanidine derivative is usually within a range of from $-50°$ C. to $150°$ C., preferably within a range of from $-30°$ C. to $120°$ C. If the reaction temperature is high, it is likely that the heat generation cannot be controlled, and a side-reaction may take place, and if the reaction temperature is too low, the reaction rate tends to be low, and the reaction time tends to be long. Further, the reaction temperature is preferably controlled in two stages.

With respect to the reaction pressure in the above reaction, the reaction may be carried under any of reduced pressure, normal pressure and elevated pressure, but it is preferably within a range of from 0.01 to 1 MPa, more preferably from 0.05 to 0.3 MPa.

The reaction time in the above reaction may vary depending upon the reaction temperature, the state of the reaction system, etc., but it is usually within a range of from 1 minute to 48 hours, preferably from 1 minute to 24 hours, more preferably from 5 minutes to 10 hours.

In order to separate the desired phosphazenium salt from the reaction solution of the above reaction, a common method composed of a combination of conventional means is employed. The separation method is not particularly limited, as the separation method varies depending upon the type of the salt to be formed, the type or amount of the solvent used, etc. For example, the desired salt may be obtained by removing a byproduct hydrogen halide salt of a guanidine derivative by a method such as washing, extraction, filtration or the like. In a case where a byproduct salt is included in the desired salt, it may be, as it is or after being re-dissolved, extracted with a suitable another solvent to separate it from the byproduct. Further, purification may be carried out by re-crystallization or column chromatography, as the case requires.

In order to convert the obtained halogen anion to a salt with another anion species, ion exchange may be carried out by a common method such as a method of treatment with a salt of an alkali metal cation and a desired anion, or a method by means of an ion exchange resin.

By subjecting an alkylene oxide to ring-opening polymerization in the presence of the above-described catalyst of the present invention, a polyalkylene glycol is produced.

Otherwise, in the present invention, a polyalkylene glycol may be produced by adding an alkylene oxide after mixing and heat-treating the phosphazenium salt represented by the above formula (1) and an active hydrogen compound, and subjecting the alkylene oxide to ring-opening polymerization.

That is, it is considered that by the above heat treatment, a salt of a phosphazenium cation represented by the above formula (2) and an anion of the active hydrogen compound Y (i.e. the catalyst of the present invention) is formed from the phosphazenium salt represented by the above formula (1) and the active hydrogen compound, whereby it becomes easy to control the temperature for the reaction of an alkylene oxide, and a polyalkylene oxide can be prepared simply and efficiently.

The above heat treatment can be carried out under the same conditions as in the method for producing the catalyst of the present invention, but is preferably carried out under a reduced pressure of at most 1.3 kPa at a temperature of at least $60°$ C. for at least 1 hour.

The alkylene oxide to be used in the method for producing a polyalkylene glycol of the present invention may, for example, be an epoxy compound such as ethylene oxide, propylene oxide, 1,2-butylene oxide, 2,3-butylene oxide, styrene oxide or cyclohexene oxide. Among them, ethylene oxide, propylene oxide, 1,2-butylene oxide or styrene oxide is preferred, and ethylene oxide or propylene oxide is more preferred.

In the method for producing a polyalkylene glycol of the present invention, the above alkylene oxides may be used alone or in combination as a mixture of two or more of them. In a case where two or more alkylene oxides are used in combination, a combination of propylene oxide and ethylene oxide is particularly preferred. In a case where a plurality of alkylene oxides are to be used in combination, it is possible to employ a method of adding them simultaneously, a method of adding them sequentially, or a method of repeating sequential addition.

In the method for producing a polyalkylene glycol of the present invention, the manner of the ring-opening polymerization reaction is not particularly limited. For example, the phosphazenium salt represented by the above formula (1) and the active hydrogen compound Y are heat-treated to prepare a salt of the phosphazenium cation represented by the above formula (2) and the active hydrogen compound anion, which is charged into a reactor after applying treatment to remove the active hydrogen compound Y which usually remains and, if necessary, a byproduct, from the obtained reaction solution, and if a solvent is to be used, such a solvent is further charged, followed by a method of supplying an alkylene oxide all at once, or a method of supplying the alkylene oxide intermittently or continuously.

In the method for producing a polyalkylene glycol of the present invention, the reaction temperature for the ring-opening polymerization reaction varies depending upon the type or amount of the phosphazenium salt represented by the above formula (1), the active hydrogen compound or the salt of a phosphazenium cation and an active hydrogen compound anion, represented by the above formula (2) and can hardly be defined, but if exemplified, it is usually at most $150°$ C., preferably within a range of from 20 to $130°$ C., more preferably from 80 to $130°$ C., particularly preferably from 90 to $110°$ C.

In the method for producing a polyalkylene glycol of the present invention, the pressure during the ring-opening polymerization reaction varies depending upon the type or amount of the alkylene oxide to be used, the phosphazenium salt represented by the above formula (1), the active hydrogen compound or the salt of a phosphazenium cation and an active hydrogen compound anion, represented by the formula (2), or the polymerization temperature, etc., but it is usually at most 3 MPa, preferably within a range of from 0.01 to 1.5 MPa, more preferably from 0.1 to 1.0 MPa, as the pressure during the polymerization reaction. The reaction time varies depending upon the type or amount of the alkylene oxide to be used or the catalyst material, or the polymerization temperature or pressure, but it is usually at most 40 hours, preferably from 0.1 to 30 hours, more preferably from 0.5 to 24 hours.

In the method for producing a polyalkylene glycol of the present invention, the catalyst of the present invention may be used in combination with a conventional initiator for the purpose of e.g. reducing a load for removing the initiator after the polymerization.

In the method for producing a polyalkylene glycol of the present invention, a solvent may be used as the case requires, in the ring-opening polymerization reaction of an alkylene oxide. The solvent to be used is not particularly limited so long as it does not hinder the ring-opening polymerization reaction. Specifically, it may, for example, be an aliphatic hydrocarbon such as pentane, hexane, heptane or cyclohexane, an aromatic hydrocarbon such as benzene or toluene, an ether such as diethyl ether, tetrahydrofuran, 1,3-dioxane or anisol, or an aprotic polar solvent such as dimethylsulfoxide, N,N-dimethylformamide, hexamethylphosphoramide or N,N'-dimethylimidazolidinone.

In the method for producing a polyalkylene glycol of the present invention, the polymerization reaction of the alkylene oxide may be carried out in the presence of an inert gas such as nitrogen or argon, as the case requires.

By the method for producing a polyalkylene glycol of the present invention, it is possible to produce a high molecular weight polyalkylene glycol having a hydroxy value of from 60 to 4 mgKOH/g and a molecular weight (number average molecular weight) of from 3,000 to 50,000, preferably a high molecular weight polyalkylene glycol having a hydroxy value of from 40 to 9 mgKOH/g and a molecular weight (number average molecular weight) of from 4,500 to 20,000.

Further, the polyalkylene glycol obtained by the method for producing a polyalkylene glycol of the present invention exhibits a low total unsaturation value of at most 0.07 meq./g. In addition, the obtained polyalkylene glycol has a narrow molecular weight distribution (Mw/Mn) of at most 1.1 and thus has excellent physical properties as a polyalkylene glycol.

The polyalkylene glycol obtained by the method for producing a polyalkylene glycol of the present invention may sometimes be used, as it is, as a starting material for a polyurethane foam or an elastomer, or as a surfactant, simply by removing a solvent when the solvent was used in the polymerization reaction. However, usually, it is treated with a mineral acid such as hydrochloric acid, phosphoric acid or sulfuric acid, an organic carboxylic acid such as formic acid, acetic acid or propionic acid, carbon dioxide, or an acid-form ion exchange resin, and then may be used as the above starting material or the surfactant. Further, a common purification may be carried out such as washing with water, an organic solvent or a mixture thereof.

EXAMPLES

Now, the present invention will be described in further detail with reference to Examples. However, it should be understood that the present invention is by no means thereby restricted. In the following Examples, the NMR spectrum, GC-MS and the hydroxy value were measured as follows.

Measurement of NMR Spectrum:

The measurement was made by means of a nuclear magnetic resonance spectrum-measuring apparatus (tradename: GSX270WB, manufactured by JEOL Ltd.) by using tetramethylsilane (TMS) as the internal standard and deuterated chloroform as a deuterated solvent.

Measurement of Number Average Molecular Weight:

A standard polystyrene-calculated value was obtained from an elution curve as measured by means of gel permeation chromatography (GPC) (tradename: HLC8020GPC, manufactured by TOSOH CORPORATION) by using tetrahydrofuran as a solvent at 40° C.

Measurement of GC-MS:

The measurement was carried out by means of a gas chromatography mass analyzer (tradename: JMS-700, manufactured by JEOL Ltd.) by using "FAB$_+$" as the ionization mode.

Measurement of Hydroxy Value and Total Unsaturation Value:

Measured in accordance with the measuring methods disclosed in JIS K1557.

Ethylene Oxide Content:

Calculated based on the proton ratio of the peak attributable to the polyol obtained by means of nuclear magnetic resonance spectrum-measuring apparatus (tradename: GSX270WB, manufactured by JEOL Ltd.)

Initiation Materials to be Used:

polyalkylene glycol A: a glycerol-type polypropylene glycol having a molecular weight of 400, polyalkylene glycol B: a propylene glycol-type polypropylene glycol having a molecular weight of 400, polyalkylene glycol C: a glycerol-type polypropylene glycol having a molecular weight of 1,000.

Preparation Example 1

Tetrakis(tetramethylguanidino)phosphonium chloride: $[(Me_2N)_2C=N]_4P^+Cl^-$ (wherein Me represents a methyl group, and the same applies hereinafter) was prepared as follows.

Into a 300 ml four-necked flask provided with a thermometer, a dropping funnel, a condenser and a magnetic stirrer, 4.01 g (10.0 mmol) of phosphorus pentachloride was introduced, and 60 ml of dehydrated toluene (manufactured by Wako Pure Chemical Industries, Ltd.) was added thereto to obtain a slurry solution. This slurry solution was immersed in a cooling bath cooled to −30° C. by dry ice-acetone to bring the internal temperature to be −30° C., and then, with stirring strongly, 22.2 g (20 mmol) of 1,1,3,3-tetramethylguanidine was dropwise added from the dropping funnel over a period of 1 hour. Stirring was continued at −30° C. for 1 hour, and then, the cooling bath was removed, and the temperature was slowly raised to room temperature. This slurry solution was further heated at 100° C. for 10 hours to obtain a white slurry solution. After cooling to room temperature, the slurry was filtrated, and the filtration residue was washed with acetone. The acetone solution was concentrated, followed by extraction by means of chloroform and water. The chloroform phase was dried over sodium sulfate. After the drying, chloroform was removed to obtain 7.9 g of tetrakis(tetramethylguanidino)phosphonium salt: $[(Me_2N)_2C=N]_4P^+Cl^-$ as a white powder. The yield was 78%.

Results of $^1$H-NMR measurement (deuterated solvent: CDCl$_3$, internal standard: tetramethylsilane):

Chemical shift: 2.83 ppm (methyl group).

Results of GC-MS (FAB+) Measurement:

m/z=487 (agreed to tetrakis(tetramethylguanidino)phosphonium cation).

The results of the elemental analysis of the product are shown in Table 1.

TABLE 1

| | Elemental analysis (wt %) | | |
|---|---|---|---|
| | C | H | N |
| Theoretical values | 46.0 | 9.2 | 32.2 |
| Measured values | 46.0 | 9.0 | 32.3 |

Preparation Example 2

Tetrakis(tetramethylguanidino)phosphonium hydroxide: [(Me$_2$N)$_2$C=N]$_4$P$^+$OH$^{31}$ was prepared as follows.

3.2 g (6 mmol) of tetrakis[(dimethylamino)imino]phosphonium chloride was dissolved in 100 ml of deionized water to prepare a 0.06 mol/L solution. This solution was passed through a column (diameter: 30 mm, height: 600 mm) packed with 100 ml of a hydroxy group-type anion exchange resin (AMBERLITE IRA4100H, manufactured by Organo Corporation) at room temperature at a flow rate of 300 ml/hr, and 150 ml of deionized water was further passed therethrough at the same flow rate. The effluent was concentrated and evaporated to dryness at 40° C. under 1 mmHg to obtain 3.1 g of tetrakis(tetramethylguanidino)phosphonium hydroxide: [(Me$_2$N)$_2$C=N]$_4$P$^+$OH$^-$ as white crystals. The yield was 99%.

Results of $^1$H-NMR measurement (deuterated solvent: CDCl$_3$, internal standard: tetramethylsilane):
Chemical shift: 2.83 ppm (methyl group).

Results of GC-MS (FAB+) Measurement:
m/z=487 (agreed to tetrakis(tetramethylguanidino)phosphonium cation).

The results of the elemental analysis of the product are shown in Table 2.

TABLE 2

| | Elemental analysis (wt %) | | |
|---|---|---|---|
| | C | H | N |
| Theoretical values | 47.6 | 9.7 | 33.3 |
| Measured values | 47.3 | 9.4 | 33.3 |

Preparation Example 3

Tetrakis(1,3-diisopropylimidazolidineimino)phosphonium chloride was prepared as follows.

Into a 200 ml four-necked flask provided with a thermometer, a dropping funnel, a condenser and a magnetic stirrer, 2.3 g (11 mmol) of phosphorus pentachloride was introduced, and 23 ml of dehydrated toluene (manufactured by Wako Pure Chemical Industries, Ltd.) was added thereto to obtain a slurry solution. This slurry solution was immersed in a cooling bath cooled to −30° C. by dry ice-acetone to bring the internal temperature to be −30° C., and then, with stirring strongly, 18.5 g (110 mmol) of 1,3-diisopropylimidazolidineimine was dropwise added from the dropping funnel over a period of 1 hour. Stirring was continued at −30° C. for 1 hour, and then, the cooling bath was removed, and the temperature was slowly raised to room temperature. This slurry solution was further heated at 100° C. for 10 hours to obtain a white slurry solution. After cooling to room temperature, the slurry was filtrated, and the filtration residue was washed with acetone. The acetone solution was concentrated, followed by extraction by means of chloroform and water. The chloroform phase was dried over sodium sulfate. After the drying, chloroform was removed to obtain 5.5 g of tetrakis(1,3-diisopropylimidazolidineimino)phosphonium salt as a white powder. The yield was 67%.

Results of $^1$H-NMR measurement (deuterated solvent: CDCl$_3$, internal standard: tetramethylsilane):
Chemical shift: 1.04 ppm (48H,d,methyl), 3.28 ppm (16H, s,methylene), 4.46 ppm (m,8H,methine).

Results of GC-MS (FAB+) Measurement:
m/z=704 (agreed to tetrakis(1,3-diisopropylimidazolidineimino)phosphonium cation).

Preparation Example 4

Tetrakis(1,3-diisopropylimidazolidineimino)phosphonium hydroxide was prepared as follows.

1.5 g (2 mmol) of tetrakis(1,3-diisopropylimidazolidineimino)phosphonium chloride was dissolved in 200 ml of deionized water to prepare a 0.01 mol/L solution. This solution was passed through a column (diameter: 30 mm, height: 600 mm) packed with 50 ml of a hydroxy group-type anion exchange resin (AMBERLITE IRA4100H, manufactured by Organo Corporation) at room temperature at a flow rate of 200 ml/hr, and 150 ml of deionized water was further passed therethrough at the same flow rate. The effluent was concentrated and then evaporated to dryness at 40° C. under 1 mmHg to obtain 1.5 g of tetrakis(1,3-diisopropylimidazolidineimino)phosphonium hydroxide as white crystals. The yield was 98%.

Results of $^1$H-NMR measurement (deuterated solvent: CDCl$_3$, internal standard: tetramethylsilane):
Chemical shift: 1.04 ppm (48H,d,methyl), 3.28 ppm (16H, s,methylene), 4.46 ppm (m,8H,methine).

Results of GC-MS (FAB+) Measurement:
m/z=704 (agreed to tetrakis(1,3-diisopropylimidazolidineimino)phosphonium cation).

Preparation Example 5

Tetrakis(1,3-dimethylimidazolidineimino)phosphonium chloride was prepared as follows.

Into a 200 ml four-necked flask provided with a thermometer, a dropping funnel, a condenser and a magnetic stirrer, 2.3 g (11 mmol) of phosphorus pentachloride was introduced, and 40 ml of dehydrated toluene (manufactured by Wako Pure Chemical Industries, Ltd.) was added thereto to obtain a slurry solution. This slurry solution was immersed in a cooling bath cooled to −30° C. by dry ice-acetone to bring the internal temperature to be −30° C., and then, with stirring strongly, 13 g (110 mmol) of 1,3-dimethylimidazolidineimine was dropwise added from the dropping funnel over a period of 1 hour. Stirring was continued at −30° C. for 1 hour, and then, the cooling bath was removed, and the temperature was slowly raised to room temperature. This slurry solution was further heated at 100° C. for 10 hours to obtain a white slurry solution. After cooling to room temperature, the slurry was filtrated, and the filtration residue was washed with acetone. The acetone solution was concentrated, followed by extraction by means of dichloromethane and water. The dichloromethane phase was dried over sodium sulfate. After drying, dichloromethane was removed to obtain 4.7 g of tetrakis(1,3-dimethylimidazolidineimino)phosphonium salt as a white powder. The yield was 84%.

Results of $^1$H-NMR measurement (deuterated solvent: CDCl$_3$, internal standard: tetramethylsilane):
Chemical shift: 2.91 ppm (24H, methyl group), 3.39 ppm (16H, methylene group).

Results of GC-MS (FAB+) Measurement:
m/z=479 (agreed to tetrakis(1,3-diisopropylimidazolidineimino)phosphonium cation).

Preparation Example 6

Tetrakis(1,3-dimethylimidazolidineimino)phosphonium hydroxide was prepared as follows.

2.0 g (4 mmol) of tetrakis(1,3-dimethylimidazolidineimino)phosphonium chloride was dissolved in 40 ml of deionized water to prepare a 0.1 mol/L solution. This solution was passed through a column (diameter: 30 mm, height: 600 mm) packed with 40 ml of a hydroxy group-type anion exchange resin (AMBERLITE RA410OH, manufactured by Organo Corporation) at room temperature at a flow rate of 150 ml/hr, and 150 ml of deionized water was further passed therethrough at the same flow rate. The effluent was concentrated and then evaporated to dryness at 40° C. under 1 mmHg to obtain 1.9 g of tetrakis(1,3-dimethylimidazolidineimino)phosphonium hydroxide as white crystals. The yield was 99%.

Results of $^1$H-NMR measurement (deuterated solvent: $CDCl_3$, internal standard: tetramethylsilane):
Chemical shift: 2.91 ppm (24H, methyl group), 3.39 ppm (16H, methylene group).

Results of GC-MS (FAB+) Measurement:
m/z=479 (agreed to tetrakis(1,3-dimethylimidazolidineimino)phosphonium cation).

Preparation Example 7

5.04 g of the phosphonium hydroxide prepared in Preparation Example 2 and 5 g of polyalkylene glycol C were mixed, and heat treatment was carried out at 80° C. under a reduced pressure of 1.3 kPa for 3 hours. Water formed by the treatment was collected, and as a result, it was 0.18 g. From this result, it was found that 2 equivalents of the phosphonium salt was reacted to the polyalkylene glycol C, and 9.8 g of a catalyst of the above formula (2) wherein n=1.5 (n≥1) was obtained.

Preparation Example 8

5.04 g of the phosphonium hydroxide prepared in Preparation Example 2 and 3.3 g of polyalkylene glycol C were mixed, and heat treatment was carried out at 80° C. under a reduced pressure of 1.3 kPa for 3 hours. Water formed by the treatment was collected, and as a result, it was 0.18 g. From this result, it was found that 3 equivalents of the phosphonium salt was reacted to the polyalkylene glycol C, and 8.2 g of a catalyst of the formula (2) wherein n=3 was obtained.

Preparation Example 9

5.04 g of the phosphonium hydroxide prepared in Preparation Example 2 and 10 g of polyalkylene glycol C were mixed, and heat treatment was carried out at 80° C. under a reduced pressure of 1.3 kPa for 3 hours. Water formed by the treatment was collected, and as a result, it was 0.18 g. From this result, it was found that 3 equivalents of the phosphonium salt was reacted to the polyalkylene glycol C, and 14.8 g of a catalyst of the formula (2) wherein n=1 was obtained.

Preparation Example 10

5.04 g of the phosphonium hydroxide prepared in Preparation Example 2 and 2 g of polyalkylene glycol B were mixed, and heat treatment was carried out at 80° C. under a reduced pressure of 1.3 kPa for 3 hours. Water formed by the treatment was collected, and as a result, it was 0.18 g. From this result, it was found that 2 equivalents of the phosphonium salt was reacted to the polyalkylene glycol B, and 6.9 g of a catalyst of the formula (2) wherein n=2 was obtained.

Preparation Example 11

5.04 g of the phosphonium hydroxide prepared in Preparation Example 2 and 0.3 g of glycerol were mixed, and heat treatment was carried out at 80° C. under a reduced pressure of 1.3 kPa for 3 hours. Water formed by the treatment was collected, and as a result, it was 0.18 g. From this result, it was found that 3 equivalents of the phosphonium salt was reacted to glycerol, and 5.1 g of a catalyst of the formula (2) wherein n=1 was obtained.

Preparation Example 12

5.04 g of the phosphonium hydroxide prepared in Preparation Example 2 and 0.9 g of glycerol were mixed, and heat treatment was carried out at 80° C. under a reduced pressure of 1.3 kPa for 3 hours. Water formed by the treatment was collected, and as a result, it was 0.18 g. From this result, it was found that 1 equivalent of the phosphonium salt was reacted to glycerol, and 5.7 g of a catalyst of the formula (2) wherein n=1 was obtained.

Example 1

0.2 g (0.4 mmol) of the phosphazenium salt [in the above formula (1), each of $R_1$ and $R_2$ is a methyl group, and $X^-$ is a hydroxy anion] obtained in Preparation Example 2 and 4.0 g (10 mmol) of polyalkylene glycol A were charged into a glass autoclave having an effective capacity of 200 ml and equipped with a thermocouple, a pressure gauge, a stirrer and an alkylene oxide-supply tube. Then, the interior of the reactor was substituted by dry nitrogen, the temperature was raised to 80° C., and heat treatment was carried out under reduced pressure for 3 hours.

After the heat treatment, the pressure was returned to normal pressure by nitrogen, the temperature was raised to 90° C., and while 30 g of propylene oxide was intermittently supplied into the reactor so as to maintain the reaction pressure to be at most 0.3 MPa, the reaction was carried out at 90° C. for 6 hours. The content was cooled to room temperature, and then returned to normal pressure to obtain 31 g of colorless and odorless polyoxypropylene triol. The obtained polyoxypropylene triol had a hydroxy value of 37 mgKOH/g and a total unsaturation value of 0.028 meq/g, and the molecular weight distribution (Mw/Mn) obtained by GPC was 1.03.

Comparative Example 1

The operation was carried out in the same manner as for the polymerization reaction in Example 1 except that 5 mmol of potassium hydroxide was used instead of the phosphazenium salt used in Example 1, and the reaction temperature was 105° C. The content was cooled to room temperature and then returned to normal pressure to obtain 30 g of colorless and odorless polyoxypropylene triol. The obtained polyoxypropylene triol had a hydroxy value of 39 mgKOH/g and a total unsaturation value of 0.114 meq/g, and the molecular weight distribution (Mw/Mn) obtained by GPC was 1.7.

Example 2

0.2 g (0.4 mmol) of the phosphazenium salt prepared in Preparation Example 2 and 4.0 g (4 mmol) of polyalkylene glycol C were charged into a glass autoclave having an effective capacity of 200 ml and equipped with a thermocouple, a pressure gauge, a stirrer and an alkylene oxide-supply tube. Then, the interior of the reactor was substituted by dry nitrogen, the temperature was raised to 80° C., and heat treatment was carried out under reduced pressure for 3 hours.

After the heat treatment, the pressure was returned to normal pressure by nitrogen, the temperature was raised to 90° C., and while 78 g of propylene oxide was intermittently supplied into the reactor so as to maintain the reaction pressure to be at most 0.3 MPa, the reaction was carried out within a temperature range of from 88 to 92° C. for 6 hours. The pressure was returned to normal pressure by nitrogen, and the content was cooled to room temperature to obtain 78 g of colorless and odorless polyoxypropylene triol. The obtained polyoxypropylene triol had a hydroxy value of 8 mgKOH/g and a total unsaturation value of 0.067 meq/g, and the molecular weight distribution (Mw/Mn) was 1.05.

Example 3

0.2 g (0.4 mmol) of the phosphazenium salt prepared in Preparation Example 2 and 4.0 g (10 mmol) of polyalkylene glycol A were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and heat treatment was carried out under reduced pressure for 3 hours.

After the heat treatment, the pressure was raised to 90° C., and while 72 g of propylene oxide was intermittently supplied into the reactor so as to maintain the reaction pressure to be at most 0.3 MPa, the reaction was carried out within a temperature range of from 88 to 92° C. for 6 hours. The pressure was returned to normal pressure by nitrogen, and the content was cooled to room temperature. Remaining propylene oxide was removed under reduced pressure, and then, 74 g of colorless and odorless polyoxypropylene triol was obtained. The obtained polyoxypropylene triol had a hydroxy value of 22 mgKOH/g and a total unsaturation value of 0.072 meq/g, and the molecular weight distribution (Mw/Mn) was 1.05.

Example 4

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and heat treatment was carried out under reduced pressure for 3 hours.

After the heat treatment, the temperature was raised to 90° C., and while 55 g of propylene oxide was intermittently supplied into the reactor so as to maintain the reaction pressure to be at most 0.3 MPa, the reaction was carried out within a temperature range of from 88 to 92° C. for 6 hours. The pressure was returned to normal pressure by nitrogen, and the content was cooled to room temperature. Remaining propylene oxide was removed under reduced pressure, and then, 61 g of colorless and odorless polyoxypropylene triol was obtained. The obtained polyoxypropylene triol had a hydroxy value of 20 mgKOH/g and a total unsaturation value of 0.028 meq/g, and the molecular weight distribution (Mw/Mn) was 1.04.

Example 5

0.2 g (0.4 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and heat treatment was carried out under reduced pressure for 3 hours.

After the heat treatment, the temperature was raised to 90° C., and while 55 g of propylene oxide was intermittently supplied into the reactor so as to maintain the reaction pressure to be at most 0.3 MPa, the reaction was carried out within a temperature range of from 88 to 92° C. for 7.5 hours. The pressure was returned to normal pressure by nitrogen, and the content was cooled to room temperature. Remaining propylene oxide was removed under reduced pressure, and then, 65 g of colorless and odorless polyoxypropylene triol was obtained. The obtained polyoxypropylene triol had a hydroxy value of 21 mgKOH/g and a total unsaturation value of 0.026 meq/g, and the molecular weight distribution (Mw/Mn) was 1.05.

Example 6

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 46 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied at 90° C. so as to bring the reaction pressure to be at most 0.4 MPa (gauge). After supplying ethylene oxide, aging was carried out at the same temperature for 2 hours. After the aging, the pressure was returned to normal pressure by nitrogen, and the content was cooled to room temperature. Remaining ethylene oxide was removed under reduced pressure, and then, 63 g of colorless and odorless polyalkylene oxide was obtained. The obtained polyalkylene oxide had an ethylene oxide content of 15.1 wt %, a hydroxy value of 22 mgKOH/g and a total unsaturation value of 0.026 meq/g, and the molecular weight distribution (Mw/Mn) was 1.05.

Example 7

0.15 g (0.2 mmol) of the phosphazenium salt prepared in Preparation Example 4 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 55 g of propylene oxide was intermittently supplied so as to maintain the reaction pressure to be at most 0.3 MPa, the reaction was carried out within a temperature range of from 88 to 92° C. for 6 hours. The pressure was returned to normal pressure by nitrogen, and the content was cooled to room temperature. Remaining propylene oxide was removed under reduced pressure, and then, 64 g of colorless and odorless polyoxypropylene triol was obtained. The obtained polyoxypropylene triol had a hydroxy value of 22 mgKOH/g and a total unsaturation value of 0.024 meq/g, and the molecular weight distribution (Mw/Mn) was 1.06.

Example 8

0.1 g (0.2 mmol) of the phosphazenium salt prepared in Preparation Example 6 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 58 g of propylene oxide was intermittently supplied so as to maintain the reaction pressure to be at most 0.3 MPa, the reaction was carried out within a temperature range of from 88 to 92° C. for 6 hours. The pressure was returned to normal pressure by nitrogen, and the content was cooled to room temperature. Remaining propylene oxide was removed under reduced pressure, and then, 65 g of colorless and odorless polyoxypropylene triol was obtained. The obtained polyoxypropylene triol had a hydroxy value of 22 mgKOH/g and a total unsaturation value of 0.025 meq/g, and the molecular weight distribution (Mw/Mn) was 1.05.

Example 9

0.8 g (0.4 mmol) of the phosphazenium salt prepared in Preparation Example 7 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and heating was carried out under reduced pressure for 3 hours.

After the dehydration treatment, the temperature was raised to 90° C., and while 60 g of propylene oxide was intermittently supplied into the reactor so as to maintain the reaction pressure to be at most 0.3 MPa, the reaction was carried out within a temperature range of from 88 to 92° C. for 7.5 hours. The pressure was returned to normal pressure by nitrogen, and the content was cooled to room temperature. Remaining propylene oxide was removed under reduced pressure, and then, 67 g of colorless and odorless polyoxypropylene triol was obtained. The obtained polyoxypropylene triol had a hydroxy value of 20 mgKOH/g and a total unsaturation value of 0.025 meq/g, and the molecular weight distribution (Mw/Mn) was 1.04.

Example 10

0.8 g (0.4 mmol) of the phosphazenium salt prepared in Preparation Example 7 and 3.5 g (8.7 mmol) of polyalkylene glycol A were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and heating was carried out under reduced pressure for 3 hours.

After the dehydration treatment, the temperature was raised to 90° C., and while 65 g of propylene oxide was intermittently supplied into the reactor so as to maintain the reaction pressure to be at most 0.35 MPa, the reaction was carried out within a temperature range of from 88 to 92° C. for 7.5 hours. The pressure was returned to normal pressure by nitrogen, and the content was cooled to room temperature. Remaining propylene oxide was removed under reduced pressure, and then, 66 g of colorless and odorless polyoxypropylene triol was obtained. The obtained polyoxypropylene triol had a hydroxy value of 20 mgKOH/g and a total unsaturation value of 0.027 meq/g, and the molecular weight distribution (Mw/Mn) was 1.04.

Example 11

0.5 g (0.2 mmol) of the phosphazenium salt prepared in Preparation Example 7 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 48 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied so that the reaction pressure became at most 0.45 MPa (gauge). The pressure was returned to normal pressure by nitrogen, and the content was cooled to room temperature. Remaining ethylene oxide was removed under reduced pressure, and then, 67 g of colorless and odorless polyalkylene oxide was obtained. The obtained polyalkylene oxide had an ethylene oxide content of 14.9 wt %, a hydroxy value of 22 mgKOH/g and a total unsaturation value of 0.024 meq/g, and the molecular weight distribution (Mw/Mn) was 1.06.

Example 12

0.3 g (0.2 mmol) of the phosphazenium salt prepared in Preparation Example 8 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 48 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied so that the reaction pressure became at most 0.4 MPa (gauge). The pressure was returned to normal pressure by nitrogen, and the content was cooled to room temperature. Remaining ethylene oxide was removed under reduced pressure, and then, 66 g of colorless and odorless polyalkylene oxide was obtained. The obtained polyalkylene oxide had an ethylene oxide content of 15.3 wt %, a hydroxy value of 23 mgKOH/g and a total unsaturation value of 0.024 meq/g, and the molecular weight distribution (Mw/Mn) was 1.05.

Example 13

0.3 g (0.2 mmol) of the phosphazenium salt prepared in Preparation Example 10 and 3.5 g (8.7 mmol) of polyalkylene glycol B were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 48 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied so that the reaction pressure became at most 0.4 MPa (gauge). The pressure was returned to normal pressure by nitrogen, and the content was cooled to room temperature. Remaining ethylene oxide was removed under reduced pressure, and then, 63 g of colorless and odorless polyalkylene oxide was obtained. The obtained polyalkylene oxide had an ethylene oxide content of 14.5 wt %, a hydroxy value of 17 mgKOH/g and a total unsaturation value of 0.024 meq/g, and the molecular weight distribution (Mw/Mn) was 1.07.

Comparative Example 2

The operation was carried out in the same manner as in Example 2 except that 0.8 mL (0.4 mmol) of a 0.5 mol/L hexane solution of a phosphazene catalyst 1-tert-butyl-4,4,4-tris(dimethylamino)-2,2-bis[tris(dimethylamino)phosphoranilideneamino]-2λ5,4λ5-catenadi(phosphazene) was used instead of 0.2 g (0.4 mmol) of the phosphazenium salt obtained in Preparation Example 2. The temperature was raised to 90° C., and propylene oxide was intermittently supplied so as to maintain the reaction pressure to be at most 0.3 MPa. At that time, propylene oxide was supplied slowly in order to control the temperature at 90° C., but due to heat absorption at the time of supplying propylene oxide or heat generation by the reaction heat, the reaction temperature fluctuated between 88 and 95° C., whereby it was difficult to control the temperature. Further, in order to control the temperature within the above range, the supply rate was further reduced, and as a result, the reaction time became 7 hours i.e. longer by 1 hour than in Example 1.

Then, the pressure was returned to normal pressure by nitrogen, and the content was cooled to room temperature. Remaining propylene oxide was removed under reduced pressure, and then, 74 g of colorless and odorless polyoxypropylene triol was obtained. The obtained polyoxypropylene triol had a hydroxy value of 25 mgKOH/g and the total unsaturation value of 0.072 meq/g, and the molecular weight distribution (Mw/Mn) was 1.11.

Example 14

0.3 g (0.2 mmol) of the phosphazenium salt prepared in Preparation Example 9 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 55 g of propylene oxide was intermittently supplied so as to maintain the reaction pressure to be at most 0.3 MPa, the reaction was carried out within a temperature range of from 88 to 92° C. for 6 hours. Then, the pressure was returned to normal pressure by nitrogen, and the content was cooled to room temperature. Remaining propylene oxide was removed under reduced pressure, and then, 52 g colorless and odorless polyalkylene oxide was obtained. The obtained polyalkylene oxide had a hydroxy value of 28 mgKOH/g and a total unsaturation value of 0.031 meq/g, and the molecular weight distribution (Mw/Mn) was 1.06.

Example 15

0.3 g (0.2 mmol) of the phosphazenium salt prepared in Preparation Example 9 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 55 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After removal of propylene oxide, 12 g of ethylene oxide was supplied so that the reaction pressure became at most 0.4 MPa (gauge). The pressure was returned to normal pressure by nitrogen, and the content was cooled to room temperature. Remaining ethylene oxide was removed under reduced pressure, and then, 51 g of colorless and odorless polyalkylene oxide was obtained. The obtained polyalkylene oxide had an ethylene oxide content of 13.1 wt %, a hydroxy value of 25 mgKOH/g and a total unsaturation value of 0.030 meq/g, and the molecular weight distribution (Mw/Mn) was 1.07.

Example 16

0.6 g (0.4 mmol) of the phosphazenium salt prepared in Preparation Example 11 and 5.0 g (54 mmol) of glycerol were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 65 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour, and then 64 g of colorless and odorless polyalkylene oxide was obtained. The obtained polyalkylene oxide had a hydroxy value of 150 mgKOH/g, a total unsaturation value of 0.005 meq/g, and the molecular weight distribution (Mw/Mn) was 1.07.

Example 17

0.24 g (0.4 mmol) of the phosphazenium salt prepared in Preparation Example 12 and 5.0 g (54 mmol) of glycerol were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 55 g of propylene oxide was intermittently supplied so as to maintain the reaction pressure to be at most 0.3 MPa, the reaction was carried out within a temperature range of from 88 to 95° C. for 8 hours. Then, remaining propylene oxide was removed under reduced pressure at 90° C. over a period of 1 hour, and then 54 g of colorless and odorless polyalkylene oxide was obtained. The obtained polyalkylene oxide had a hydroxy value of 156 mgKOH/g, a total unsaturation value of 0.011 meq/g, and the molecular weight distribution (Mw/Mn) was 1.07.

Preparation Example 13

Preparation of tetrakis[(dimethylamino)imino]phosphonium chloride $[(Me_2N)_2C=N]_4P^+Cl^-$ (wherein Me represents a methyl group, the same applies hereinafter)

Into a 300 ml four-necked flask provided with a thermometer, a dropping funnel, a condenser and a magnetic stirrer, 4.01 g (10.0 mmol) of phosphorus pentachloride was introduced, and 60 ml of dehydrated toluene (manufactured by Wako Pure Chemical Industries, Ltd.) was added thereto to obtain a slurry solution. This slurry solution was immersed in a cooling bath cooled to −30° C. by dry ice-acetone to bring the internal temperature to be −30° C., and then, with stirring strongly, 22.2 g (20 mmol) of tetramethylguanidine was dropwise added from the dropping funnel over a period of 1 hour. Stirring was continued at −30° C. for 1 hour, and then, the cooling bath was removed, and the temperature was slowly raised to room temperature. Further, this slurry solution was heated at 100° C. for 10 hours to obtain a white slurry solution. After cooling to room temperature, the slurry was filtrated, and the filtration residue was washed with acetone. The acetone solution was concentrated to obtain 9.6 g of tetrakis[(dimethylamino)imino]phosphonium salt: $[(Me_2N)_2C=N]_4P^+Cl^-$. The yield was 98%.
Results of $^1$H-NMR measurement (deuterated solvent: CDCl$_3$, internal standard: tetramethylsilane):
Chemical shift: 2.51 ppm (24H, methyl group).
Results of GC-MS (FAB+) Measurement:
m/z=487 (agreed to tetrakis[(dimethylamino)imino]phosphonium cation).

The results of the elemental analysis of the product are shown in Table 3.

TABLE 3

| | Elemental analysis (wt %) | | |
|---|---|---|---|
| | C | H | N |
| Theoretical values | 46.0 | 9.2 | 32.2 |
| Measured values | 46.0 | 9.0 | 32.3 |

Preparation Example 14

Preparation of tetrakis[(dimethylamino)imino]phosphonium hydroxide

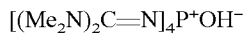

3.2 g (6 mmol) of tetrakis[(dimethylamino)imino]phosphonium chloride was dissolved in 100 ml of deionized water to prepare a 0.06 mol/L solution. This solution was passed through a column (diameter: 30 mm, height: 600 mm) packed with 100 ml of a hydroxy group-type anion exchange resin (tradename: AMBERLITE IRA410OH, manufactured by Organo Corporation) at room temperature at a flow rate of 300 ml/hr, and 150 ml of deionized water was further passed therethrough at the same flow rate. The effluent was concentrated and then evaporated to dryness at 40° C. under 1 mmHg to obtain 3.1 g of tetrakis[tris(dimethylamino)imino]phosphonium hydroxide: $[(Me_2N)_2C=N]_4P^+OH^-$ as white crystals. The yield was 99%.
Results of $^1$H-NMR measurement (deuterated solvent: CDCl$_3$, internal standard: tetramethylsilane):
Chemical shift: 2.51 ppm (methyl group).
Results of GC-MS (FAB+) Measurement:
m/z=487 (agreed to tetrakis[(dimethylamino)imino]phosphonium cation).
The results of the elemental analysis of the product are shown in Table 4.

TABLE 4

| | Elemental analysis (wt %) | | |
|---|---|---|---|
| | C | H | N |
| Theoretical values | 47.6 | 9.7 | 33.3 |
| Measured values | 47.3 | 9.4 | 33.3 |

Example 18

0.2 g (0.4 mmol) of the phosphazenium salt [in the above formula (1), each of R$_1$ and R$_2$ is a methyl group, and X$^-$ is a hydroxy anion] obtained in Preparation Example 14 and 5.0 g (58 mmol) of glycerol were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours. After the dehydration treatment, the pressure was returned to normal pressure by nitrogen, and while 48 g of propylene oxide was intermittently supplied at 90° C. so as to maintain the reaction pressure to be at most 0.3 MPa, the reaction was carried out for 6 hours. The content was cooled to room temperature, and 33 g of colorless and odorless liquid polyoxypropylene triol was obtained. The obtained polyoxypropylene triol had a hydroxy value of 131 mgKOH/g.

Example 19

0.2 g (0.4 mmol) of the phosphazenium salt [in the above formula (1), each of $R_1$ and $R_2$ is a methyl group, and $X^-$ is a hydroxy anion] obtained in Preparation Example 14 and 4.0 g (10 mmol) of polyalkylene glycol A were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the pressure was returned to normal pressure by nitrogen, the temperature was raised to 90° C., and while 30 g of propylene oxide was intermittently supplied so as to maintain the reaction pressure to be at most 0.3 MPa, the reaction was carried out at 90° C. for 6 hours. The content was cooled to room temperature, and then, the pressure was returned to normal pressure. 31 g of colorless and odorless polyoxypropylene triol was obtained. The obtained polyoxypropylene triol had a hydroxy value of 37 mgKOH/g and a total unsaturation value of 0.03 meq/g, and the molecular weight distribution obtained by GPC was 1.03.

Comparative Example 3

The operation was carried out in the same manner as for the polymerization reaction in Example 18 except that the phosphazenium salt used in Example 19 was not employed. Propylene oxide was not consumed at all, and the content in the reactor was 4.01 g, which was substantially equal to the weight of the glycerol charged into the reactor itself, and no polyoxypropylene triol was obtained.

Example 20

1.0 g (2 mmol) of the phosphazenium salt prepared in Preparation Example 14 and 4.0 g (10 mmol) of polyalkylene glycol B were charged into a glass autoclave having an effective capacity of 200 ml and equipped with a temperature-measuring tube, a pressure gauge, a stirrer and an alkylene oxide-supply tube. The interior of the reactor was substituted by dry nitrogen, the temperature was raised to 90° C., and while 38 g of propylene oxide was intermittently supplied so as to maintain the reaction pressure to be at most 0.3 MPa, the reaction was carried out within a temperature range of from 88 to 92° C. for 6 hours. Then, the pressure was returned to normal pressure by nitrogen, and the content was cooled to room temperature. 39 g of colorless and odorless polyoxypropylene diol was obtained. The obtained polyoxypropylene diol had a hydroxy value of 32 mgKOH/g.

Example 21

0.2 g (0.4 mmol) of the phosphazenium salt prepared in Preparation Example 14 and 4.0 g (10 mmol) of polyalkylene glycol A were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under reduced pressure for 3 hours.

After the dehydration treatment, the temperature was raised to 90° C., and while 72 g of propylene oxide was intermittently supplied so as to maintain the reaction pressure to be at most 0.3 MPa, the reaction was carried out within a temperature range of from 88 to 92° C. for 6 hours. Then, the pressure was returned to normal pressure by nitrogen, and the content was cooled to room temperature. Remaining propylene oxide was removed under reduced pressure, and then, 74 g of colorless and odorless polyoxypropylene triol was obtained. The obtained polyoxypropylene triol had a hydroxy value of 22 mgKOH/g.

Example 22

0.2 g (0.4 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under a reduced pressure of 0.2 kPa for 3 hours.

After the dehydration treatment, the temperature was raised to 100° C., and while 58 g of propylene oxide was intermittently supplied so as to maintain the reaction pressure to be at most 0.3 MPa, the reaction was carried out within a temperature range of from 98 to 102° C. for 6 hours. Then, the pressure was returned to normal pressure by nitrogen, and the content was cooled to room temperature. The remaining propylene oxide was removed under reduced pressure, and then, 64 g of colorless and odorless polyoxypropylene triol was obtained. The obtained polyoxypropylene triol had a hydroxy value of 24 mgKOH/g.

Example 23

The operation was carried out in the same manner as in Example 22 except that the reaction was carried out within a temperature range of from 78 to 82° C. for 6 hours. 28 g of colorless and odorless polyoxypropylene triol was obtained. The obtained polyoxypropylene triol had a hydroxy value of 56 mgKOH/g.

Example 24

The operation was carried out in the same manner as in Example 22 except that the reaction was carried out within a temperature range of from 108 to 112° C. for 6 hours. 66 g of colorless and odorless polyoxypropylene triol was obtained. The obtained polyoxypropylene triol had a hydroxy value of 23 mgKOH/g.

Example 25

The operation was carried out in the same manner as in Example 22 except that the reaction was carried out within a temperature range of from 118 to 122° C. for 6 hours. 44 g of colorless and odorless polyoxypropylene triol was obtained. The obtained polyoxypropylene triol had a hydroxy value of 40 mgKOH/g.

Example 26

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under a reduced pressure of 0.2 kPa for 3 hours.

After the dehydration treatment, the temperature was raised to 90° C., and while 58 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, ethylene oxide was supplied at 90° C. so that the reaction pressure became at most 0.4 MPa. After supplying ethylene oxide, aging was carried out at the same temperature for 2 hours. After the aging, the pressure was returned to normal pressure by nitrogen, and the content was cooled to room temperature. Remaining ethylene oxide was removed under reduced pressure, and then, 64 g of colorless and odorless polyalkylene oxide was obtained. The obtained polyalkylene oxide had an ethylene oxide content of 15.8 wt % and a hydroxy value of 22 mgKOH/g.

Example 27

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under a reduced pressure of 0.2 kPa for 3 hours.

After the dehydration treatment, the temperature was raised to 90° C., and while 46 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied at 90° C. so that the reaction pressure became at most 0.4 MPa. After supplying ethylene oxide, aging was carried out at the same temperature for 2 hours. After the aging, the pressure was returned to normal pressure by nitrogen, and the content was cooled to room temperature. Remaining ethylene oxide was removed under reduced pressure, and then, 58 g of colorless and odorless polyalkylene oxide was obtained. The obtained polyalkylene oxide had an ethylene oxide content of 9.4 wt % and a hydroxy value of 27 mgKOH/g.

Example 28

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under a reduced pressure of 0.2 kPa for 3 hours.

After the dehydration treatment, the temperature was raised to 90° C., and while 46 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 24 g of ethylene oxide was supplied at 90° C. so that the reaction pressure became at most 0.4 MPa. After supplying ethylene oxide, aging was carried out at the same temperature for 2 hours. After the aging, the pressure was returned to normal pressure by nitrogen, and the content was cooled to room temperature. Remaining ethylene oxide was removed under reduced pressure, and then, 65 g of colorless and odorless polyalkylene oxide was obtained. The obtained polyalkylene oxide had an ethylene oxide content of 32.6 wt % and a hydroxy value of 20 mgKOH/g.

Example 29

0.3 g (0.4 mmol) of the phosphazenium salt prepared in Preparation Example 4 and 3.5 g (8.7 mmol) of polyalkylene glycol A were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and heating was carried out under a reduced pressure of 0.2 kPa for 3 hours.

After the dehydration treatment, the temperature was raised to 90° C., and while 65 g of propylene oxide was intermittently supplied into the reactor so as to maintain the reaction pressure to be at most 0.3 MPa, the reaction was carried out within a temperature range of from 88 to 92° C. for 7.5 hours. Then, the pressure was returned to normal pressure by nitrogen, and the content was cooled to room temperature. Remaining propylene oxide was removed under reduced pressure, and then, 64 g of colorless and odorless polyoxypropylene triol was obtained. The obtained polyoxypropylene triol had a hydroxy value of 22 mgKOH/g.

Example 30

0.15 g (0.2 mmol) of the phosphazenium salt prepared in Preparation Example 4 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 80° C., and dehydration treatment was carried out under a reduced pressure of 0.2 kPa for 3 hours.

After the dehydration treatment, the temperature was raised to 90° C., and while 46 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 11 g of ethylene oxide was supplied at 90° C. so that the reaction pressure became at most 0.4 MPa. The pressure was returned to normal pressure by nitrogen, and the content was cooled to room temperature. Remaining ethylene oxide was removed under a reduced pressure of 0.2 kPa, and then, 64 g of colorless and odorless polyalkylene oxide was obtained. The obtained polyalkylene oxide had an ethylene oxide content of 14.8 wt % and a hydroxy value of 22 mgKOH/g.

Example 31

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 100° C., and dehydration treatment was carried out under a reduced pressure of 1.3 kPa for 3 hours.

After the dehydration treatment, the temperature was adjusted to 90° C., and while 46 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied at 90° C. so that the reaction pressure became at most 0.4 MPa. After supplying ethylene oxide, aging was carried out at the same temperature for 2 hours. After the aging, the pressure was returned to normal pressure by nitrogen, and the content was cooled to room temperature. Remaining ethylene oxide was removed under reduced pressure, and then, 63 g of colorless and odorless polyalkylene oxide was obtained. The obtained polyalkylene oxide had an ethylene oxide content of 14.5 wt % and a hydroxy value of 22 mgKOH/g.

Example 32

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 100° C., and dehydration treatment was carried out under a reduced pressure of 0.2 kPa for 1 hour.

After the dehydration treatment, the temperature was adjusted to 90° C., and while 46 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. After the removal of propylene oxide, 12 g of ethylene oxide was supplied at 90° C. so that the reaction pressure became at most 0.4 MPa. After supplying ethylene oxide, aging was carried out at the same temperature for 2 hours. After the aging, the pressure was returned to normal pressure by nitrogen, and the content was cooled to room temperature. Remaining ethylene oxide was removed under reduced pressure, and then, 53 g of colorless and odorless polyalkylene oxide was obtained. The obtained polyalkylene oxide had an ethylene oxide content of 15.5 wt % and a hydroxy value of 33 mgKOH/g.

Example 33

0.1 g (0.2 mmol) of the phosphazenium salt prepared in Preparation Example 2 and 8.7 g (8.7 mmol) of polyalkylene glycol C were charged into a glass autoclave having an effective capacity of 200 ml and equipped with a temperature-measuring tube, a pressure gauge, a stirrer and an alkylene oxide-supply tube. Then, the interior of the reactor was substituted by dry nitrogen, the temperature was raised to 60° C., and dehydration treatment was carried out under a reduced pressure of 0.2 kPa for 5 hours.

After the dehydration treatment, the temperature was raised to 90° C., and while 48 g of propylene oxide was intermittently supplied so as to maintain the reaction pressure to be at most 0.3 MPa, the reaction was carried out within a temperature range of from 88 to 92° C. for 6 hours. Then, remaining propylene oxide was removed under reduced pressure at 90° C. over a period of 1 hour. The pressure was returned to normal pressure by nitrogen, and the content was cooled to room temperature to obtain 55 g of colorless and odorless polyalkylene oxide. The obtained polyalkylene oxide had a hydroxy value of 28 mgKOH/g.

Comparative Example 4

The operation was carried out in the same manner as in Example 21 except that 0.2 g (0.4 mmol) of the phosphazenium salt obtained in Preparation Example 13 was used instead of 0.2 g (0.4 mmol) of the phosphazenium salt obtained in Preparation Example 14. The temperature was raised to 90° C., and propylene oxide was intermittently supplied so as to maintain the reaction pressure to be at most 0.3 MPa. The obtained polyol had substantially the same weight as the polyol A before the initiation, and the reaction did not proceed at all.

Comparative Example 5

The operation was carried out in the same manner as in Comparative Example 2 except that 0.3 g (0.4 mmol) of tetrakis[tris(dimethylamino)phosphoranilideneamino]-phosphonium hydroxide was used instead of 0.8 mL (0.4 mmol) of a 0.5 mol/L hexane solution of phosphazene catalyst 1-tert-butyl-4,4,4-tris(dimethylamino)-2,2-bis[tris(dimethylamino)phosphoranilideneamino]-2$\lambda$5,4$\lambda$5-catenadi (phosphazene). The temperature was raised to 90° C., and propylene oxide was intermittently supplied so as to maintain the reaction pressure to be at most 0.3 MPa.

At that time, propylene oxide was slowly supplied in order to carry out the temperature control at 90° C., but due to heat absorption at the time of supplying propylene oxide or heat generation by the reaction heat, the reaction temperature fluctuated between 88 and 95° C., whereby it was difficult to control the temperature. Further, in order to control the temperature within the above range, the supply rate was further reduced, and as a result, the reaction time became 8 hours i.e. longer by 2 hours than in Example 18.

As is evident from the foregoing Examples and Comparative Examples, in the method for producing a polyalkylene glycol of the present invention, it is easy to control the temperature during the reaction.

Industrial Applicability

The polyalkylene glycol producing catalyst of the present invention can easily be synthesized, and does not contain special metal components. Further, in the method for producing a polyalkylene glycol using such a polyalkylene glycol producing catalyst, it is easy to control the temperature during the reaction of an alkylene oxide, and it is possible to produce a polyalkylene oxide having a narrow molecular weight distribution and having a high molecular weight and a low total unsaturation value simply and efficiently without leaving any odor. Thus, the industrial applicability of the present invention is high.

The entire disclosures of Japanese Patent Application No. 2008-257286 filed on Oct. 2, 2008 and Japanese Patent Application No. 2008-296909 filed on Nov. 20, 2008 including specifications, claims and summaries are incorporated herein by reference in their entireties.

The invention claimed is:

1. A polyalkylene glycol producing catalyst which is composed of a salt of a phosphazenium cation and an active hydrogen compound anion, represented by the following formula (2):

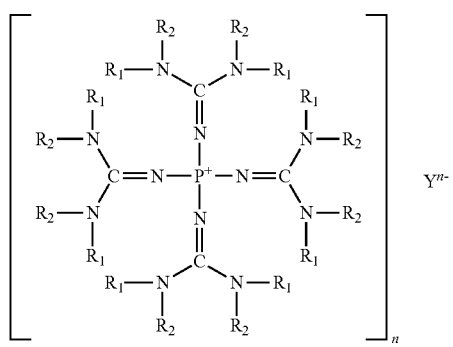

[in the above formula (2), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, n is a real number of from 2 to 8, and $Y^{n-}$ is an anion of an active hydrogen compound which is obtained by removing n protons from an active hydrogen compound Y].

2. The polyalkylene glycol producing catalyst according to claim 1, wherein in the phosphazenium cation represented by the formula (2), each of $R_1$ and $R_2$ is a methyl group, or $R_1$ is a methyl group or an isopropyl group and $R_2$'s are bonded to each other to form a dimethylene group thereby to form a ring structure.

3. The polyalkylene glycol producing catalyst according to claim 1, wherein the active hydrogen compound Y is a compound selected from an organic compound having a partial structural formula of —OH or —NH—.

4. The polyalkylene glycol producing catalyst according to claim 3, wherein the organic compound having a partial structural formula of —OH is one or more members selected from the group consisting of a $C_{2-20}$ polyhydric alcohol having from 2 to 8 hydroxy groups, a saccharide or its derivative, and a polyalkylene oxide having from 2 to 8 terminals, having from 2 to 8 hydroxy groups at the terminals and having a number average molecular weight of from 200 to 20,000.

5. The polyalkylene glycol producing catalyst according to claim 3, wherein the organic compound having a partial structural formula of —NH— is one or more members selected from the group consisting of a $C_{2-20}$ polyvalent amine having 2 or 3 primary or secondary amino groups, and a $C_{4-10}$ cyclic polyvalent amine having 2 or 3 secondary amino groups.

6. A method for producing the polyalkylene glycol producing catalyst as defined in claim 1, which comprises mixing a phosphazenium salt represented by the following formula (1):

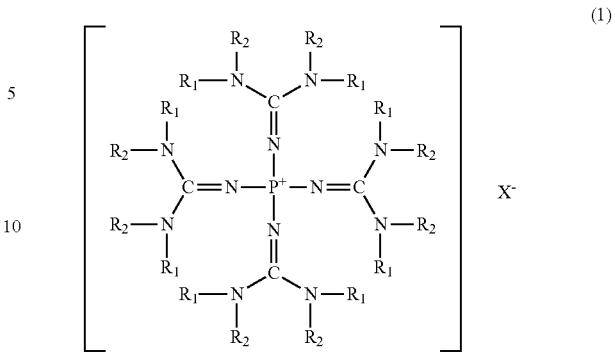

[in the above formula (1), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, and $X^-$ is a hydroxy anion, an alkoxy anion or a carboxy anion] and an active hydrogen compound Y, followed by heat treatment.

7. The method for producing the polyalkylene glycol producing catalyst according to claim 6, wherein in the phosphazenium salt represented by the formula (1), each of $R_1$ and $R_2$ is a methyl group, or $R_1$ is a methyl group or an isopropyl group and $R_2$'s are bonded to each other to form a dimethylene group thereby to form a ring structure.

8. The method for producing the polyalkylene glycol producing catalyst according to claim 6, wherein $X^-$ in the phosphazenium salt represented by the formula (1) is one or more anions selected from the group consisting of a hydroxy anion, an alkoxy anion derived from a $C_{1-4}$ saturated alkyl alcohol or phenol, and a carboxy anion derived from a $C_{2-4}$ carboxylic acid.

9. The method for producing the polyalkylene glycol producing catalyst according to claim 6, wherein $X^-$ in the phosphazenium salt represented by the formula (1) is a hydroxy anion.

10. The method for producing the polyalkylene glycol producing catalyst according to claim 6, wherein the active hydrogen compound Y is water or a compound selected from an organic compound having a partial structural formula of —OH or —NH—.

11. The method for producing the polyalkylene glycol producing catalyst according to claim 10, wherein the organic compound having a partial structural formula of —OH is one or more members selected from the group consisting of a $C_{1-20}$ alcohol, a $C_{2-20}$ polyhydric alcohol having from 2 to 8 hydroxy groups, a saccharide or its derivative, and a polyalkylene oxide having from 2 to 8 terminals, having from 1 to 8 hydroxy groups at the terminals and having a number average molecular weight of from 200 to 20,000.

12. The method for producing the polyalkylene glycol producing catalyst according to claim 10, wherein the organic compound having a partial structural formula of —NH— is one or more members selected from the group consisting of a $C_{2-20}$ polyvalent amine having 2 or 3 primary or secondary amino groups, a $C_{4-10}$ saturated cyclic secondary amine, and a $C_{4-10}$ cyclic polyvalent amine having 2 or 3 secondary amino groups.

13. The method for producing the polyalkylene glycol producing catalyst according to claim 6, which comprises mixing the phosphazenium salt represented by the formula (1) and the active hydrogen compound Y within such a range that the active hydrogen compound Y is from 0.2 to 1,000 mol per 1 mol of the phosphazenium salt, followed by heat treatment.

14. A method for producing a polyalkylene glycol, which comprises subjecting an alkylene oxide to ring-opening polymerization in the presence of the polyalkylene glycol producing catalyst as defined in claim 1.

15. A method for producing a polyalkylene glycol, which comprises subjecting an alkylene oxide to ring-opening polymerization in the presence of the polyalkylene glycol producing catalyst obtained by the method as defined in claim 6.

16. A method for producing a polyalkylene glycol, which comprises mixing a phosphazenium salt represented by the following formula (1):

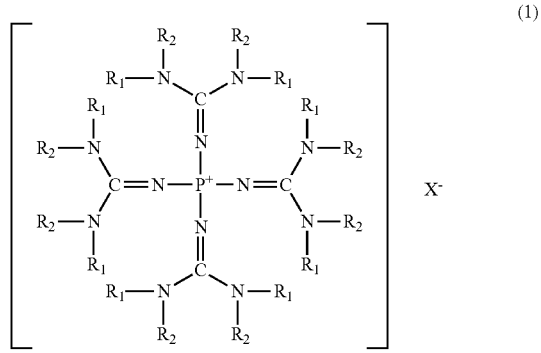

(1)

[in the above formula (1), each of $R_1$ and $R_2$ which are independent of each other, is a $C_{1-10}$ alkyl group, an unsubstituted or substituted $C_{6-10}$ phenyl group, or an unsubstituted or substituted $C_{6-10}$ phenylalkyl group, provided that $R_1$ and $R_2$, or $R_2$'s, may be bonded to each other to form a ring structure, and $X^-$ is a hydroxy anion, an alkoxy anion or a carboxy anion] and an active hydrogen compound Y, followed by heat treatment, and then adding an alkylene oxide and subjecting the alkylene oxide to ring-opening polymerization.

17. The method for producing a polyalkylene glycol according to claim 14, wherein the alkylene oxide is one or more members selected from the group consisting of ethylene oxide, propylene oxide, 1,2-butylene oxide and styrene oxide.

18. The method for producing a polyalkylene glycol according to claim 14, wherein the polyalkylene glycol has a total unsaturation value of at most 0.07 meq./g and a molecular weight distribution (Mw/Mn) of at most 1.1.

19. The method for producing a polyalkylene glycol according to claim 14, wherein the polyalkylene glycol having a hydroxyl value of at most 60 mgKOH/g and a number average molecular weight within a range of from 3,000 to 50,000.

* * * * *